(12) United States Patent
Wink et al.

(10) Patent No.: US 6,936,639 B2
(45) Date of Patent: Aug. 30, 2005

(54) NITROXYL PROGENITORS IN THE TREATMENT OF HEART FAILURE

(75) Inventors: David A. Wink, Hagerstown, MD (US); Martin Feelisch, Shreveport, LA (US); David A. Kass, Columbia, MD (US); Nazareno Paolocci, Baltimore, MD (US); Katrina Miranda, Tucson, AZ (US); Jon Fukuto, Agoura, CA (US); Tatsuo Katori, Baltimore, MD (US)

(73) Assignees: The United States of America as represented by the Secretary of the Department of Health and Human Services, Washington, DC (US); The Regents of the University of California, Oakland, CA (US); Johns Hopkins University, Baltimore, MD (US); The Board of Supervisors of Louisiana State University and Agricultural and Mechanical College, Louisiana State University Health Sciences Center, Shreveport, LA (US)

(*) Notice: Subject to any disclaimer, the term of this patent is extended or adjusted under 35 U.S.C. 154(b) by 125 days.

(21) Appl. No.: 10/226,412

(22) Filed: Aug. 21, 2002

(65) Prior Publication Data

US 2004/0039063 A1 Feb. 26, 2004

(51) Int. Cl.$^7$ .......................... A61K 31/19; A61K 31/13
(52) U.S. Cl. ........................... 514/575; 514/611
(58) Field of Search ................. 514/645, 653, 514/575, 611

(56) References Cited

U.S. PATENT DOCUMENTS

| | | |
|---|---|---|
| 4,954,526 A | 9/1990 | Keefer |
| 5,039,705 A | 8/1991 | Keefer et al. |
| 5,212,204 A | 5/1993 | Keefer et al. |
| 6,083,515 A | 7/2000 | Garvey et al. |
| 6,143,734 A | 11/2000 | Garvey et al. |
| RE37,116 E | 3/2001 | Garvey et al. |
| 6,297,260 B1 | 10/2001 | Bandarage et al. |
| 6,323,234 B1 | 11/2001 | Garvey et al. |
| 2002/0010146 A1 | 1/2002 | Garvey et al. |
| 2002/0016322 A1 | 2/2002 | Bandarage et al. |

FOREIGN PATENT DOCUMENTS

| | | |
|---|---|---|
| WO | WO 96/32946 | 4/1996 |
| WO | WO 98/43621 | 3/1998 |
| WO | WO 99/33823 | 12/1998 |
| WO | WO 00/67754 | 5/2000 |
| WO | WO 01/45703 | 12/2000 |
| WO | WO 02/060378 | 12/2001 |

OTHER PUBLICATIONS

Harrison's Principles of Internal Medicine, Isselbacher et al. eds., 13$^{th}$ ed. vol. 1, 1994, pp 1002–1008.*
Hart et al., Abstract, *Am J Physiol Heart Circ Physiol*, vol. 281, No. 1, pp. H146–H154 (Jul. 2001).
Paolocci et al., Abstract, *Italian Heart Journal*, vol. 2, Suppl. 3, p. 62S (Sep. 2001).
Paolocci et al., *PNAS*, vol. 98, No. 18, pp. 10463–10468 (Aug. 28, 2001).
Pagliaro et al., *J. Physiol.*, vol. 536, p. 143P (2001).
Ma et al., *PNAS*, vol. 96, No. 25, pp. 14617–14622 (1999).
Maragos et al., *J. Med. Chem.*, vol. 34, No. 11, pp. 3242–3247 (1991).
Fitzhugh et al., *Free Radical Biology & Medicine*, vol. 28, No. 10, pp. 1463–1469 (2000).
Pagliaro et al., Abstract 1265, *Supplement to Circulation*, vol. 104, No. 17, pp. 11–263–11–264 (2001).

* cited by examiner

Primary Examiner—Raymond J. Henley, III
(74) Attorney, Agent, or Firm—Klarquist Sparkman LLP (57) ABSTRACT

Administration of an HNO/NO$^-$ donating compound, such as Angeli's salt, increases myocardial contractility while concomitantly lowering left ventricular preload in subjects experiencing heart failure Moreover, administration of the HNO/NO$^-$ donating compound isopropylamine (IPA)/NO (Na(CH$_3$)$_2$CHNHN(O)NO) surprisingly exhibited positive inotropic effects in subjects experiencing heart failure that were superior to those caused by the HNO/NO$^-$ donating compound Angeli's salt. Additionally, in contrast to the effects observed with NO$^-$ donors, administration of an HNO/NO$^-$ donor in combination with a positive inotropic agent did not impair the positive inotropic effect of the positive inotropic agent Further, HNO/NO$^-$ exerts its positive inotropic effect independent of the adrenergic system, increasing contractility even in subjects receiving beta-antagonist therapy

16 Claims, 8 Drawing Sheets

Fig. 2. Nitroxyl contractile effects in CHF were load-independent

Fig. 6. The CGRP receptor blocker CGRP(8-37) prevents nitroxyl contractile effects in HF (n=3)

Fig. 7. CGRP levels in normal and CHF dogs, before and after stimulation with nitroxyl Fig. 8. Propranolol does not prevent nitroxyl-induced contractile effects (n=5)

NITROXYL PROGENITORS IN THE TREATMENT OF HEART FAILURE

FIELD

Pharmaceutical compounds and compositions are disclosed that are useful to treat heart failure.

BACKGROUND

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and enlarged hearts The most common cause of CHF is atherosclerosis, which causes blockages in the coronary arteries that provide blood flow to the heart muscle. Ultimately, such blockages may cause myocardial infarction with subsequent decline in heart function and resultant heart failure Other causes of CHF include valvular heart disease, hypertension, viral infections of the heart, alcohol consumption, and diabetes. Some cases of CHF occur without clear etiology and are called idiopathic. The effects of CHF on a subject experiencing the condition can be fatal.

There are several types of CHF. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal Swelling (edema) in the abdomen and legs is a typical symptom of diastolic heart failure.

CHF is also classified according to its severity The New York Heart Association classification classifies CHF into four classes:

Class I—no obvious symptoms, with no limitations on physical activity,

Class II—some symptoms during or after normal activity, with mild physical activity limitations, Class III—symptoms with less than ordinary activity, with moderate to significant physical activity limitations;

Class IV—significant symptoms at rest, with severe to total physical activity limitations Typically, a subject progresses through the classes as the subject lives with the condition.

Although CHF is generally thought of as a chronic, progressive condition, it can also develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema, and dyspnea.

Common treatment agents for CHF include, vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have recently become standard agents for treating mild to moderate heart failure. Lowes et al, *Clin. Cardiol.*, 23:III11–6 (2000).

Positive inotropic agents include beta-adrenergic agonists, such as dopamine, dobutamine, dopexamine, and isoproterenol. Dobutamine is commonly given to subjects experiencing late-stage heart failure characterized by severely reduced ventricular ejection fraction or the inability of the subject to undertake physical activity without discomfort. Dobutamine is particularly effective for treating this type of heart failure because of its cardio-selectivity. U.S. Pat. No. 4,562,206 describes dobutamine's cardio-selectivity for the beta-1 adrenergic receptor relative to its activity at the vascular alpha and beta-2 adrenergic receptors. This cardio-selectivity results in a desired positive inotropic effect without a substantial, concomitant increase or decrease in blood pressure Such blood pressure changes in subjects experiencing heart failure could cause further deterioration in heart function.

However, the use of beta-agonists has potential complications, such as arrhythmogenesis and increased oxygen demand by the heart. Additionally, the initial short-lived improvement of myocardial contractility afforded by these drugs is followed by an accelerated mortality rate resulting largely from a greater frequency of sudden death Katz, HEART FAILURE: PATHOPHYSIOLOGY, MOLECULAR BIOLOGY AND CLINICAL MANAGEMENT, Lippincott, Williams & Wilkins (1999).

Beta-antagonists antagonize beta-adrenergic receptor function. While initially contra-indicated in heart failure, they have been found to provide a marked reduction in mortality and morbidity in clinical trials. Bouzamondo et al., *Fundam. Clin. Pharmacol.*, 15: 95–109 (2001). Accordingly, they have become an established therapy for heart failure. Bouzamondo, supra However, even subjects that improve under beta-antagonist therapy may subsequently decompensate and require acute treatment with a positive inotropic agent. Unfortunately, as their name suggests, beta-antagonists block the mechanism of action of the positive inotropic beta-agonists that are used in emergency care centers. Bristow et al., *J. Card. Fail.*, 7: 8–12 (2001).

Additionally, vasodilating agents are also used to treat heart failure. Vasodilators, such as nitroglycerin, have been used for a long period of time to treat heart failure However, the cause of nitroglycerin's therapeutic effect was not known until late in the last century when it was discovered that the nitric oxide molecule (NO) was responsible for nitroglycerin's beneficial effects. In fact, the Nobel Prize was awarded in 1998 to three researchers who discovered $NO^-$'s beneficial effects. Opie & White in NITRATES IN DRUGS FOR THE HEART, W. B. Saunder, Philadephia, 33–53 (2001), explain that such compounds are useful for treating heart failure due to their balanced venous and arterial vasorelaxant effects U.S. Pat. No. 5,212,204 describes a group of NO donating compounds containing the NONO group. The patent discloses that NO donated from such compounds has vasodilative properties and can be useful to treat cardiac diseases that would respond favorably to a decrease in blood pressure, including acute congestive heart failure The patent identifies Angeli's salt (sodium trioxodinitrate or $Na_2N_2O_3$) as such a compound Angeli's salt is a compound that can decompose to donate either $NO^-$ or NO depending on the oxidation state of the environment. Fitzhugh & Keefer, *Free Radical Biology & Medicine*, 28(10) 1463–1469 (2000). For example, in the presence of oxidants such as ferricyanide, Angeli's salt decomposes to donate $NO^-$. Fitzhugh & Keefer, supra In some subjects experiencing heart failure, a nitric oxide donor is administered in combination with a positive inotropic agent to both cause vasodilation and to increase myocardial contractility However, this combined administration can impair the effectiveness of positive inotropic treatment agents For example, Hart et al, *Am. J. Physiol. Heart Circ. Pyhsiol.*, 281:146–54 (2001) reported that administration of the nitric oxide donor sodium nitroprusside, in combination with the positive inotropic, beta-adrenergic agonist dobutamine, impaired the positive intotropic effect of dobutamine Hare et al., *Circulation*, 92:2198–203 (1995) also disclosed the inhibitory effect of NO⁻ on the effectiveness of dobutamine.

Researchers have also investigated other forms of nitric oxide to determine their effects on the heart The nitroxyl species includes the nitroxyl anion (NO⁻), which is the one-electron reduction product of NO. Depending on the pH of the environment, the nitroxyl anion may be protonated to HNO. Experiments testing the effects of NO⁻ donors in cardiac diseases have demonstrated that NO⁻ can have a deleterious effect on the myocardium when given to reperfused myocardium. In fact, Ma et al., *Proc. Nat'l Acad. Sci.*, 96(25) 14617–14622 (1999) reported that administration of Angeli's salt as an NO⁻ donor to anesthetized rabbits 5 minutes prior to reperfusion (after ischemia) increased myocardial ischemia/reperfusion injury. Also, Takahira et al., *Free Radical Biology & Medicine*, 31(6) 809–815 (2001) reported that administration of Angeli's salt as an NO⁻ donor during ischemia and 5 minutes before reperfusion of rat renal tissue contributed to neutrophil infiltration into the tissue, which is believed to cause ischemia/reperfusion injury.

Patent Cooperation Treaty (PCT) international application PCT/US00/12957 discloses administering a charged nitric oxide species to offset the adverse effects of a potassium channel activator in a method of administering a potassium channel activator to prevent or treat cardiovascular disorders including, among others, congestive heart failure The only NO⁻ donors described in the application are thionitrates that form disulfide species

SUMMARY

The inventors discovered that administration of a nitroxyl (HNO/NO⁻) donating compound, such as Angeli's salt, increased myocardial contractility while it concomitantly lowered left ventricular preload in subjects experiencing heart failure Moreover, administration of the HNO/NO⁻ donating compound isopropylamine (IPA)/NO (Na(CH₃)₂CHNHN(O)NO) surprisingly exhibited positive inotropic effects in subjects experiencing heart failure that were superior to those caused by the HNO/NO⁻ donating compound Angeli's salt Additionally, in contrast to the effects observed with NO⁻ donors, administration of an HNO/NO⁻ donor in combination with a positive inotropic agent did not impair the positive inotropic effect of the positive inotropic agent. Further, the inventors discovered that HNO/NO⁻ exerts its positive inotropic effect independent of the adrenergic system, increasing contractility even in subjects receiving beta-antagonist therapy Accordingly, due to their concomitant positive inotropic/lusotropic action and unloading effects, HNO/NO⁻ donors are helpfuil in treating cardiovascular diseases characterized by high resistive load and poor contractile performance. In particular, HNO/NO⁻ donating compounds such as IPA/NO are useful treatment agents for heart failure. Moreover, these agents are useful when used in combination with other positive inotropic agents, such as beta-adrenergic agonists for example, dobutamine. Additionally, HNO/NO⁻ donors are useful for treating heart failure in subjects receiving beta-antagonist therapy.

Provided herein are methods of treating heart failure by administering a therapeutically effective dose at least one HNO/NO⁻ donating compound to a subject experiencing heart failure. Also provided are methods of administering a therapeutically effective dose of at least one HNO/NO⁻ donating compound in combination with at least one other positive inotropic agent to a subject experiencing heart failure. Further provided are methods of administering a therapeutically effective dose of at least one HNO/NO⁻ donating compound to a subject who is receiving beta-antagonist therapy and who is experiencing heart failure More particularly, methods are provided herein for administering compounds containing the N-oxy-N-nitroso group (diazeniumdolates), which donate HNO/NO⁻, to treat heart failure. Such compounds include Angeli's salt, IPA/NO, and analogs and derivatives of such compounds. Additionally, methods are provided herein for administering such compounds in combination with beta-adrenergic agonists to treat heart failure. Such agonists include dopamine, dobutamine, and isoproterenol, and analogs and derivatives of such compounds Also provided are methods of administering HNO/NO⁻ donors to subjects receiving treatment with beta-antagonizing agents such as propranolol, metoprolol, bisoprolol, bucindolol, and carvedilol Further, methods are provided herein for treating specific classifications of heart failure, such as Class III heart failure and acute heart failure.

These and other features and aspects of the disclosed methods will become more apparent and better understood with regard to the following figures and description

DETAILED DESCRIPTION

Disclosed herein is a method of treating CHF by administering a therapeutically effective dose of at least one nitroxyl (HNO/NO) donating compound to a subject experiencing heart failure. In particular embodiments the HNO/NO⁻ donating compound is IPA/NO. In other particular embodiments the HNO/NO⁻ donating compound is Piloty's acid Also disclosed herein is a method of treating CHF by administering a therapeutically effective dose of at least one HNO/NO⁻ donating compound in combination with a therapeutically effective dose of at least one positive inotropic agent to a subject experiencing heart failure. In particular embodiments the HNO/NO⁻ donating compound is a diazeniumdolate, such as IPA/NO, and the positive inotrope is a beta-adrenergic agonist, such as dobutamine Additionally, in particular embodiments of the methods described above, the HNO/NO⁻ donating compound or the combination of the HNO/NO⁻ donating compound and the positive inotropic compound are used to treat Class III CHF, or other non-acute CHF. In still other embodiments the methods are used to treat acute CHF Also disclosed is a method of treating CHF in a subject receiving beta-antagonist therapy by administering a therapeutically effective dose of at least one HNO/NO⁻ donating compound. In particular embodiments the HNO/NO⁻ donating compound is a diazeniumdolate, such as Angeli's salt.

A nitroxyl donor is an agent or compound that provides a physiologically effective amount of HNO or NO⁻ (HNO/NO⁻). The HNO/NO⁻ donating compound is any compound that donates HNO/NO⁻ and has a safety profile indicating the compound would be tolerated by a subject in the amount necessary to achieve a therapeutic effect. One of ordinary skill in the art would be able to determine the safety of administering particular compounds and dosages to live subjects. Such a compound includes any compound having the formula wherein J is an organic or inorganic moiety, $M^{+x}$ is a pharmaceutically acceptable cation, wherein x is the valence of the cation, a is 1 or 2, b and c are the smallest integers that result in a neutral compound, and wherein the compound is administered under conditions that cause it to release HNO/NO⁻. The compounds of Formula I are known generally as diazeniumdolates because they contain the N-oxy-N-nitroso complex. Angeli's salt is a compound of formula I that disassociates under physiological conditions to donate HNO/NO⁻ Other diazeniumdolates that disassociate under physiological conditions to generate HNO/NO⁻, such as IPA/NO or Sulfi/NO (N-nitrosohydroxylamine-N-sulfonate/ammonium salt), are also used in performing the method. Additionally, analogs and derivatives of such compounds can be used. Moreover, conditions, such as the oxidation state of the environment, can be altered to cause such compounds to donate HNO/NO⁻

An analog is a molecule that differs in chemical structure from a parent compound, for example a homolog (differing by an increment in the chemical structure, such as a difference in the length of an alykl chain), a molecular fragment, a structure that differs by one or more functional groups, or a change in ionization. Structural analogs are often found using quantitative structure activity relationships (QSAR), with technologies such as those disclosed in Remington: *The Science and Practice of Pharmacology*, 19$^{th}$ Edition (1995), chapter 28. A derivative is a biologically active molecule derived from the base structure.

Wang et al., "New chemical and biological aspects of S-nitrosothiols," Curr. Med. Chem., 7(8):821–34 (2000), describes NO⁻ formation from heterolytic decomposition of S-nitrosothiol compounds. Thus, S-nitrosothiol compounds such as S-nitroso-L-cystine ethyl ester, S-nitroso-L-cystine, S-nitroso-glutathione, S-nitroso-N-acetyl-cystine, S-nitroso-3-mercaptoetanol, S-nitroso-3-mercaptopropanoic acid, S-nitroso-2-aimonethanethiol, S-nitroso-N-acetyl penicillamine (SNAP), S-nitrosocaptopril, as well as others are also used in performing the provided method. In particular, S-nitrosoglutathione (GNSO) has been reported as capable of being reduced to HNO/NO⁻ in the presence of thiols. Hogg et al, Biochem. J., 323:477–481 (1997).

Piloty's acid (benzenesulfohydroxamic acid) is a hydroxamic acid (X(—O)NHOH) that donates HNO/NO⁻ and is useful in performing the provided methods. Other hydroxamic acids that donate HNO/NO⁻, in particular, other sulfohyrdroxamic acids and their derivatives are also useful Thionitrates (R—(S)—NO₂, wherein R is a polypeptide, an amino acid, a sugar, a modified or unmodified oligonucleotide, a straight or branched, saturated or unsaturated, aliphatic or aromatic, substituted or unsubstituted hydrocarbon, or a heterocylclic group) that donate HNO/NO⁻ are useful in performing the methods provided In particular, such compounds that form disulfide species are useful.

One of ordinary skill in the art would be able to determine these and other compounds capable of donating HNO/NO⁻. Also included in this term is direct administration of HNO/NO⁻.

Compositions comprising more than one HNO/NO⁻ donating compound are also used. For example, IPA/NO and another compound that dissociates to generate HNO/NO⁻ for example, Piloty's acid, are used to treat heart failure In particular embodiments the HNO/NO⁻ donating compound is administered in the form of a pharmaceutical composition. A pharmaceutical composition comprising an effective amount of the HNO/NO⁻ donating compound as an active ingredient could be easily prepared by standard procedures well known in the art, with pharmaceutically acceptable non-toxic solvents and/or sterile carriers, if necessary. Such preparations are administered orally or in injectable form, or directly to myocardial tissue. In other embodiments the HNO/NO⁻ donor is administered without a pharmaceutical carrier. In particular embodiments the HNO/NO⁻ donor is administered by a short-term infusion, such as for 5 to 20 minutes. In other embodiments the HNO/NO⁻ donor is administered by a long-term infusion, such as from 3–4 hours. The HNO/NO⁻ donated by Angeli's salt retains its beneficial effects during 3–4 hours of perfusion.

The dose of the HNO/NO⁻ donating compound is a therapeutically effective dose A therapeutically effective dose of an HNO/NO⁻ donating compound comprises a dose effective to increase contractility in a subject experiencing heart failure Optimizing therapy to be effective across a broad population can be performed with a careful understanding of various factors to determine the appropriate therapeutic dose, in view of the inventors' disclosure that these agents cause a positive inotropic effect as well as venous dilation. In particular embodiments, an infusion of 10 micrograms ($\mu$g)/kilogram of body weight (kg)/minute (min) is administered for 5–20 min to treat acute heart failure. In one example, the agent administered at this dose is Angeli's salt. In other embodiments an infusion of 2 5 $\mu$g/kg/min is administered for 5–20 min to treat acute heart failure. In one example, the agent administered at this dose is IPA/NO.

A positive inotrope is an agent or compound that causes an increase in myocardial contractile function. Such an agent includes a beta-adrenergic receptor agonist, an inhibitor of phophodiesterase activity, and calcium-sensitizers. Beta-adrenergic receptor agonists include, among others, dopamine, dobutamine, terbutaline, and isoproterenol Analogs and derivatives of such compounds are also used For example, U.S. Pat. No. 4,663,351 describes a dobutamine prodrug that can be administered orally One of ordinary skill in the art would be able to determine these and other compounds that are capable of causing positive inotropic effects and also additional beta-agonist compounds. In particular embodiments the beta-receptor agonist is selective for the beta-1 receptor. However, in other embodiments the beta-agonist is selective for the beta-2 receptor, or is not selective for any particular receptor. Additionally, compositions comprising more than one positive inotropic agent are used. For example, dobutamine and isoproterenol are used to treat heart failure.

In particular embodiments the positive inotropic agent is administered in combination with the HNO/NO⁻ donor. The combined administration of the HNO/NO⁻ donor and the positive inotropic agent comprises administering the HNO/NO⁻ donor either sequentially with the positive inotropic agent for example, the treatment with one agent first and then the second agent, or administering both agents at substantially the same time, wherein there is an overlap in performing the administration. With sequential administration a subject is exposed to the agents at different times, so long as some amount of the first agent, which is sufficient to be therapeutically effective in combination with the second agent, remains in the subject when the other agent is administered. Treatment with both agents at the same time can be in the same dose, such as a physically mixed dose, or in separate doses administered at the same time In particular embodiments the positive inotropic agent is administered in the form of a pharmaceutical composition. A pharmaceutical composition comprising an effective amount of the positive inotropic agent as an active ingredient could be easily prepared by standard procedures well known in the art, with pharmaceutically acceptable non-toxic solvents and/or sterile carriers, if necessary. Such preparations are administered orally or in injectable form, or directly to myocardial tissue. In other embodiments the positive inotropic agent is administered without a pharmaceutical carrier.

The dose of the positive inotropic agent is a therapeutically effective dose. In particular embodiments positive inotropic agent is administered at a dose of between 2 and 20 $\mu$g/kg/min. In certain examples dobutamine is administered at this dose. However, in other embodiments, higher and lower dosages are administered to subjects experiencing heart failure. For example, a dose of 0.5 $\mu$g/kg/min is administered, or a dose of 40 $\mu$g/kg/min is administered. Optimizing therapy to be effective across a broad population can be performed with a careful understanding of various factors to determine the appropriate therapeutic dose, in view of the inventors' disclosure that the positive inotropic agent is administered in combination with an HNO/NO⁻ donor.

In particular embodiments an HNO/NO⁻ donor is administered to a subject experiencing heart failure that is receiving beta-antagonist therapy. A beta-antagonist (also known as a beta-blocker) includes any compound that effectively acts as an antagonist at a subject's beta-adrenergic receptors, and provides desired therapeutic or pharmaceutical results, such as diminished vascular tone and/or heart rate. In particular embodiments the beta-antagonist is selective for a particular receptor, such as the beta-1 receptor. In other embodiments the beta-antagonist is not selective for any particular beta receptor. Beta-antagonizing agents include metoprolol, bisoprolol, bucindolol, carvedilol, timolol, propranolol, pindolol, and atenolol. One of ordinary skill in the art would be able to identify these and other compounds that are capable of acting as beta-adrenergic antagonists at a subject's beta-adrenergic receptors A subject who is receiving beta-antagonist therapy is any subject to whom a beta-antagonist has been administered, and in whom the beta-antagonist continues to act as an antagonist at the subject's beta-adrenergic receptors. In particular embodiments a determination of whether a subject is receiving beta-blocking therapy is made by examination of the subject's medical history. In other embodiments the subject is screened for the presence of beta-blocking agents by chemical tests, such as high-speed liquid chromatography as described in Thevis et al., *Biomed. Chromatogr.*, 15:393–402 (2001).

The administration of an HNO/NO⁻ donating compound either alone, in combination with a positive inotropic agent, or to a subject receiving beta-antagonist therapy, is used to treat heart failure of all classifications. In particular embodiments an HNO/NO⁻ donating compound is used to treat early-stage chronic heart failure, such as Class II heart failure. In other embodiments an HNO/NO⁻ donating compound is used in combination with a positive inotropic agent, such as isoproterenol to treat Class IV heart failure. In still other embodiments an HNO/NO⁻ donating compound is used in combination with a positive inotropic agent, such as isoproterenol to treat acute heart failure. In some embodiments, when HNO/NO⁻ is used to treat early stage heart failure, the dose administered is lower than that used to treat acute heart failure. In other embodiments the dose is the same as is used to treat acute heart failure.

The following are non-limiting examples of particular embodiments of the methods provided herein

EXAMPLE 1

This example demonstrates that infusion of an HNO/NO⁻ donor caused positive inotropic effects in failing myocardium. Further, infusion of an HNO/NO⁻ donor complemented the positive inotropic effect of dobutamine, as opposed to the impairment of dobutamine's positive inotropic effect observed with NO donors. Additionally, when compared with an infusion of Angeli's salt designed to cause a systemic blood pressure decrease nearly equivalent to that caused by IPA/NO, the HNO/NO⁻ donor IPA/NO exerted a stronger positive inotropic effect.

The effect of HNO/NO⁻ donated by AS (10 micrograms ($\mu$g)/kilogram (kg)/minute (min) for 5–20 min) and IPA/NO (2.5–5 0 µg/kg/min for 5–20 min) on basal cardiovascular function was tested in mongrel dogs. Studies were performed at a constant heart rate during atrial pacing (130–160 beats per minute). Myocardial effects produced by HNO/NO⁻ donating compounds were compared to those produced by the NO donors DEA/NO and nitroglycerin at doses titrated to achieve the same decline in systolic pressure (a measure of systemic blood pressure) as the HNO/NO⁻ donors Hemodynamic data was sampled at 250 Hertz (Hz) and steady-state and pressure-dimension parameters were derived. Since in vivo cardiac contractility assessment requires separation of the effects of chamber loading, pressure-volume relation indexes, specifically, the end-systolic elastance (Ees), and the slope of $dP/dt_{max}$-end-diastolic dimension ($D_{EDV}$) relations were employed. Isovolumic relaxation was derived from pressure decay waveforms assuming a nonzero decay asymptote.

Serum concentrations of nitrite and nitrate were determined by a modified Griess assay, with and without prior chemical reduction of nitrate to nitrite using $VCl_3$. Serum stored at −70° C. was deproteinized by ultrafiltration (30 kilodalton (kD) cut-off, Centricon, Sartorius) at 4° C., and absorbance at 540 nanometer (nm) read using a plate reader (Perkin Elmer HTS 7000 BioAssay Reader controlled by TECAN WinSelect software) after a 37° C. incubation with Griess reagents for 30–45 min.

Figure 1:
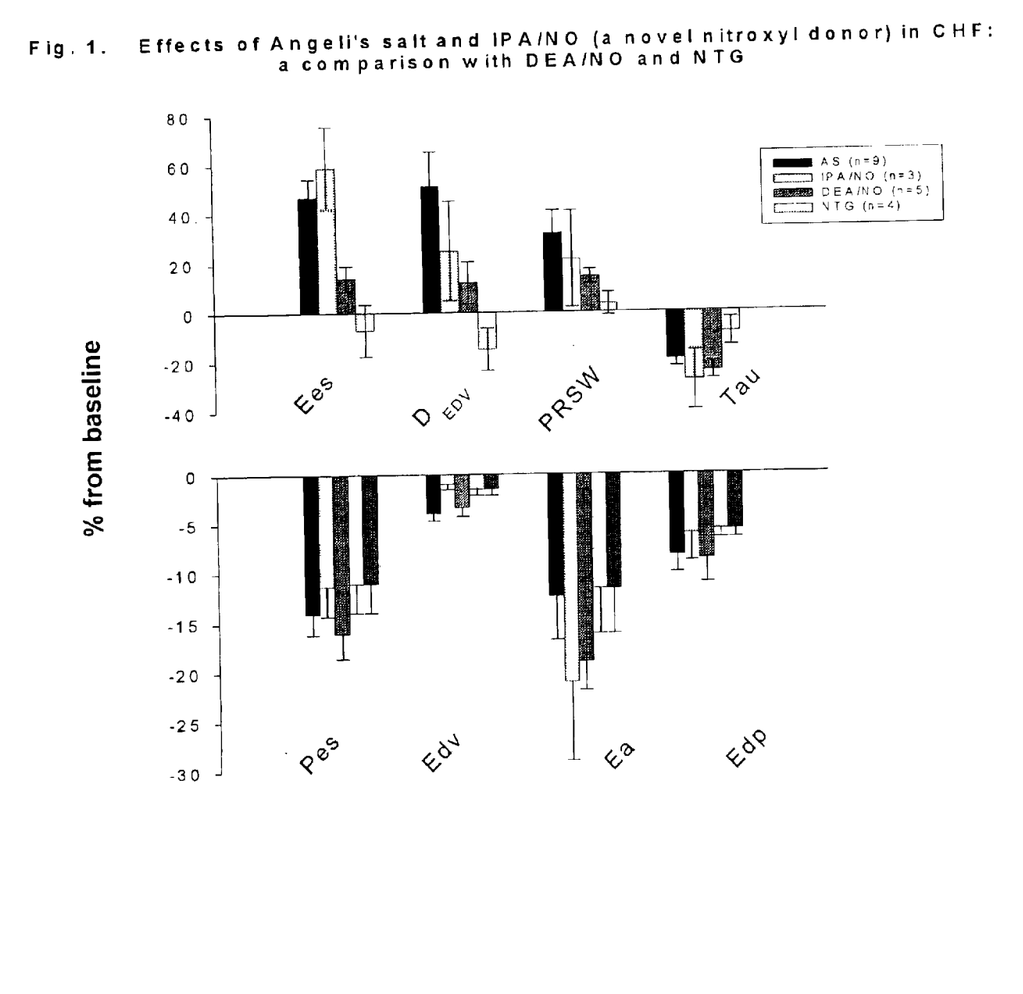
FIG. 1 shows the percentage change from a baseline for several diagnostic tests of hearts of conscious dogs experiencing congestive heart failure (CHF) resulting from administration of the HNO/NO⁻ donating compounds Angeli's salt (AS) and isoproylamine/NO (IPA/NO), as well as the NO⁻ donors diethylamine/NO (DEA/NO) and nitroglycerin (NTG) The diagnostic tests included end-systolic elastance (Ees), preload-normalized maximal change in pressure over change in time dP/dt ($D_{EDV}$), pre-load recruitable stroke work (PRSW), the time constant of ventricular relaxation (tau), end systolic pressure (Pes), end diastolic volume (Edv), arterial resistance (Ea), and end diastolic pressure (Edp).

With reference to FIG. 1, each compound tested was administered in doses titrated to achieve nearly equivalent end systolic pressures (Pes) in order to allow comparison between equivalent levels of dilation. Angeli's salt and IPA/NO caused significant increases in contractility during heart failure as measured by Ees, $D_{EDV}$, and PRSW. These increases were much greater than the small increases observed with DEA/NO and were opposite of the negative inotropic effects observed with nitroglycerin Additionally, both Angeli's salt and IPA/NO reduced the cardiac load as measured by Edv (preload) and Ea (afterload). Surprisingly, IPA/NO caused a greater increase in cardiac contractility than Angeli's salt as measured by Ees, which, being load-independent, is a good parameter for assessing myocardial contractility. This is especially surprising because the doses of IPA/NO were one-half to one-quarter the doses of Angeli's salt.

Figure 2:
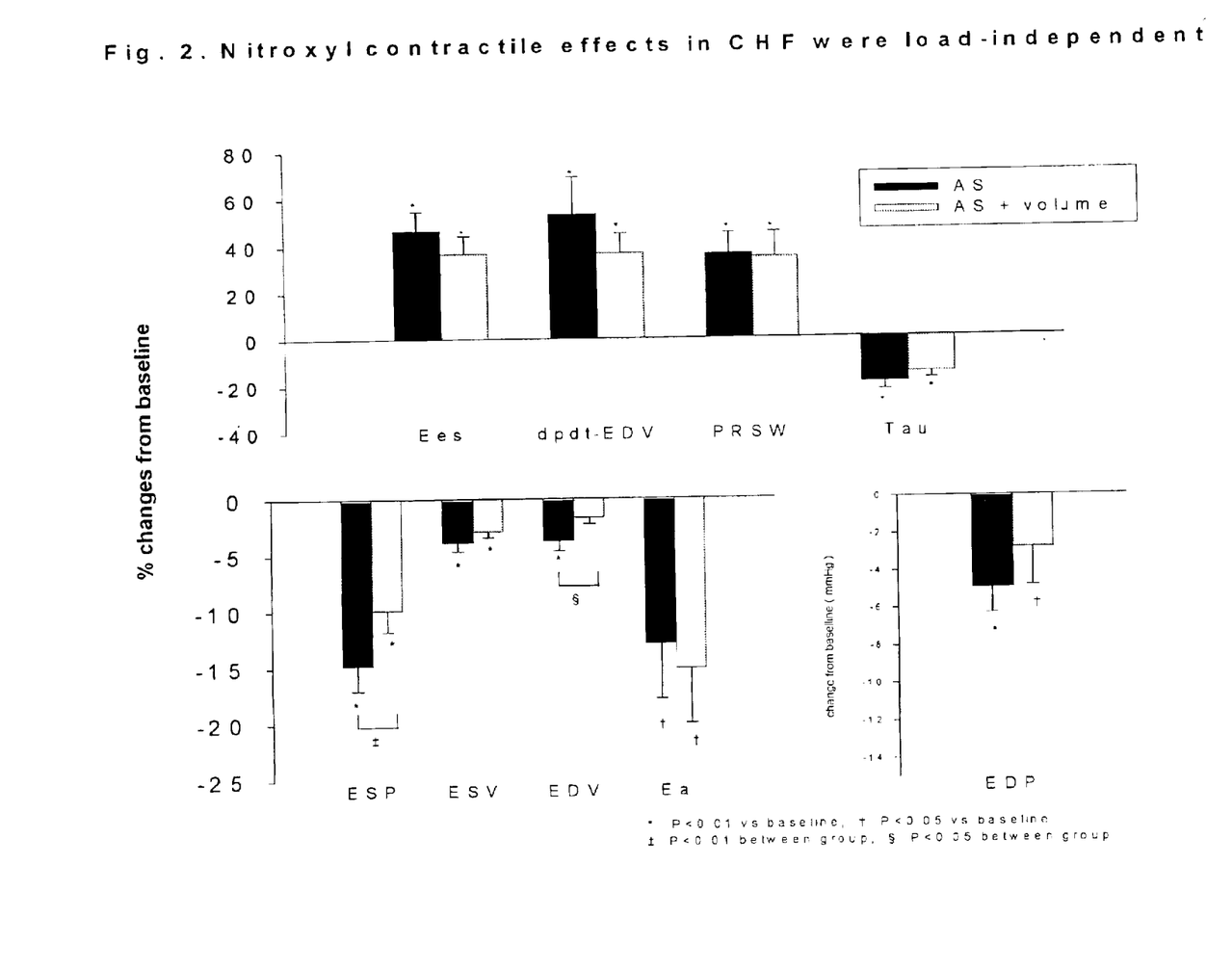
FIG. 2 shows the percentage change from a baseline for several diagnostic tests of hearts of conscious dogs experiencing CHF resulting from the administration of the HNO/NO⁻ donating compound Angeli's salt (AS), and the administration of AS when the dog hearts were under loading conditions (AS+volume). The diagnostic tests included Ees, preload-normalized maximal change in pressure over change in time dP/dt (dPdt–EDV), PRSW, tau, end systolic pressure (ESP), end systolic volume (ESV), end diastolic volume (EDV), Ea, and end diastolic pressure (EDP).
Figure 3:
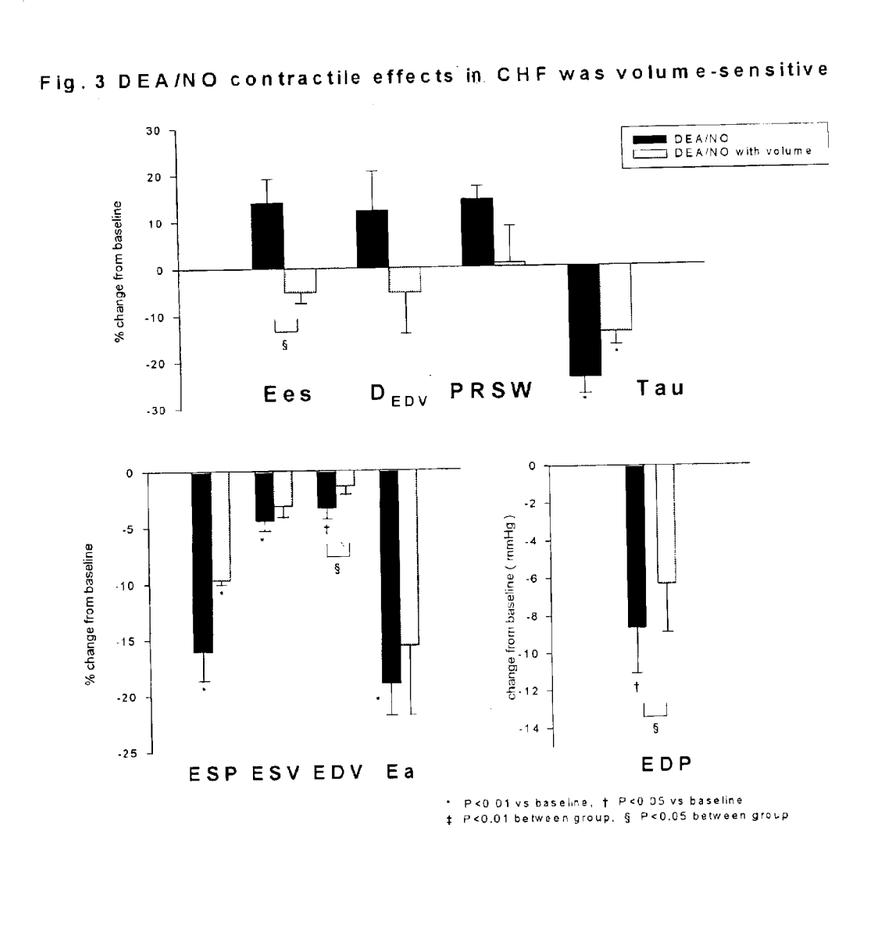
FIG. 3 shows the percentage change from a baseline for several diagnostic tests of hearts of conscious dogs experiencing CHB resulting from the administration of the NO donating compound DEA/NO and the administration of DEA/NO when the dog hearts were under a load (DEA/NO with volume). The diagnostic tests included Ees, $D_{EDV}$, PRSW, tau, ESP, ESV, EDV, Ea, and EDP.
Figure 4:
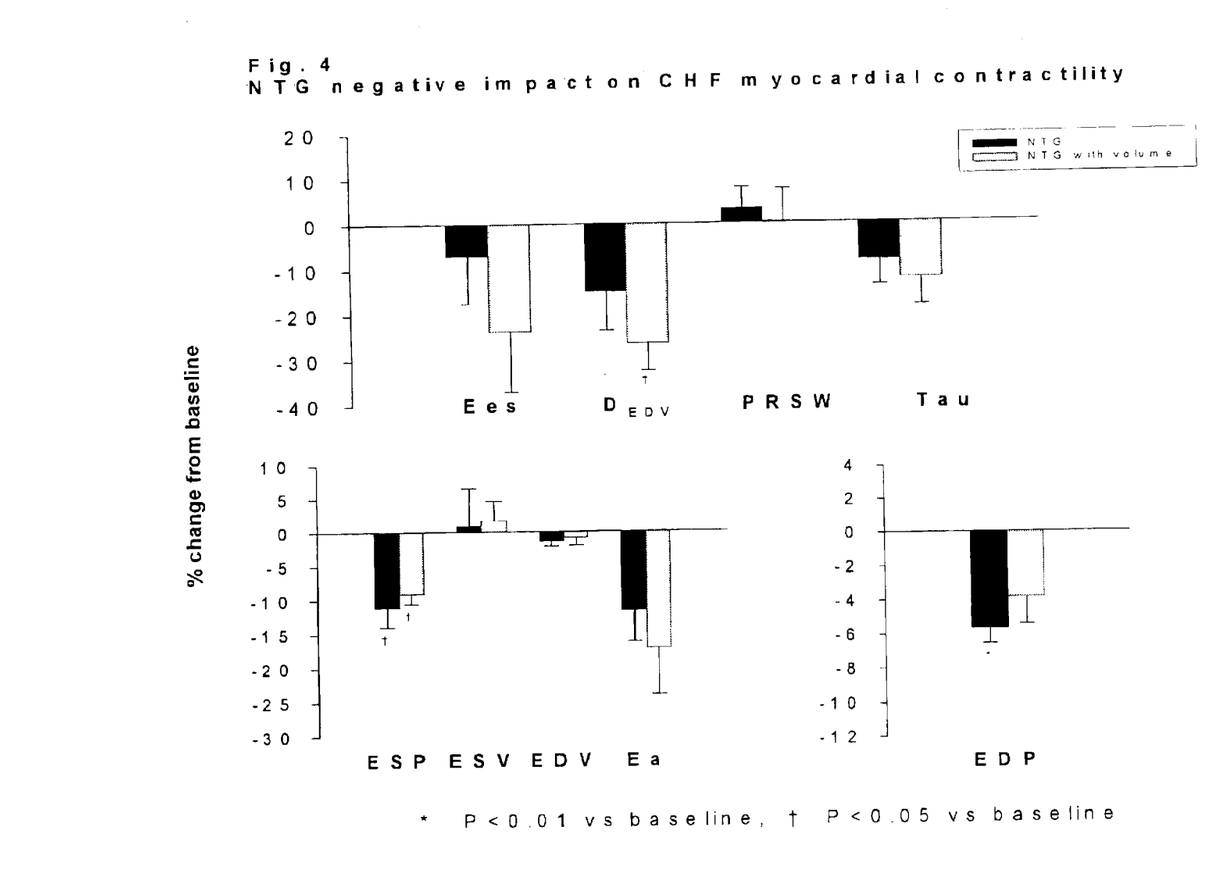
FIG. 4 shows the percentage change from a baseline for several diagnostic tests of hearts of conscious dogs experiencing CHF resulting from the administration of the NO donating compound nitroglycerin (NTG) and the administration of NTG when the dog hearts were under a load (volume loading). The diagnostic tests included Ees, $D_{EDV}$, PRSW, tau, ESP, ESV, EDV, Ea, and EDP.
Figure 5:
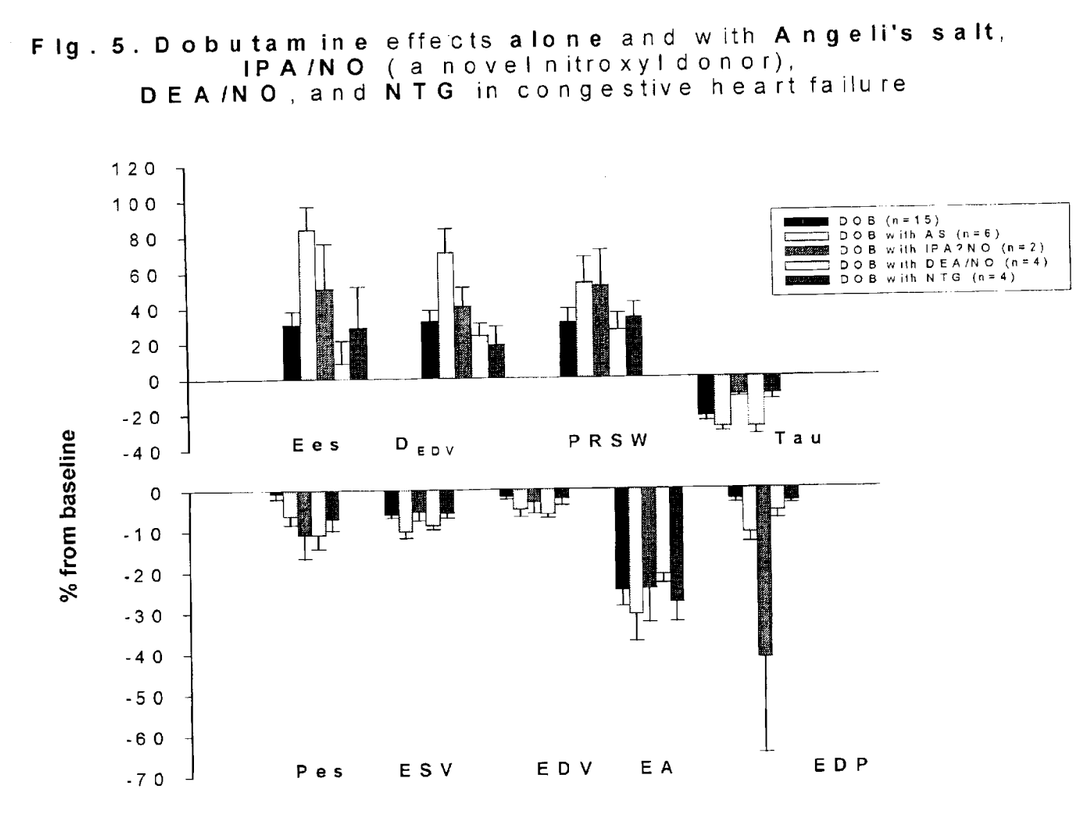
FIG. 5 shows the percentage change from a baseline for several diagnostic tests of hearts of conscious dogs experiencing CHF resulting from the administration of the positive inotropic agent dobutamine (DOB) in combination with the HNO/NO⁻ donating compounds AS and IPA/NO and the NO⁻ donating compounds DEA/NO and NTG. The diagnostic tests included Ees, $D_{EDV}$, PRSW, tau, Pes, ESV, EDV, arterial resistance (EA), and EDP.

With reference to FIG. 2, the administration of HNO/NO⁻ exhibited a positive inotropic effect, which was not dependent on cardiac load. As illustrated by the measurements of Ees and PRSW for both loaded and unloaded states, HNO/NO⁻ exerted a nearly equivalent positive inotropic effect regardless of cardiac load. This indicates that the contractility increases caused by HNO/NO⁻ are primary as opposed to secondary effects. In contrast, with reference to FIG. 3, the minor positive inotropic effects observed with the administration of NO⁻ (DEA/NO) were reversed when the heart was under cardiac load conditions, that is at matched end-diastolic volume. Moreover, FIG. 4 illustrates that administration of the NO donor nitroglycerin caused contractility to decrease when administered alone, and caused an even greater negative inotropic effect under loading conditions. This indicates that the minor contractility increase observed with DEA/NO is merely secondary to the vasodilatory effects of the compound. That is, NO has no direct positive inotropic effects because any increases in contractility were abolished upon volume repletion With reference to FIG. 5, administration of AS and IPA/NO resulted in a greater positive inotropic effect than administration of dobutamine alone. For example, administration of AS resulted in a more than doubling of Ees over administration of dobutamine alone. In contrast, administration of DEA/NO and nitroglycerin reduced the positive inotropic effect of dobutamine, as illustrated by the decrease in Ees when the dobutamine was administered with DEA/NO and NTG.

EXAMPLE 2

This example demonstrates that the positive inotropic effect of HNO/NO⁻ is a function of its stimulation of calcitonin gene-related peptide (CGRP) signaling rather than a function of beta-agonism To test the relation between the inotropic action of HNO/NO⁻ and calcitonin gene-related peptide (CGRP) signaling, CGRP receptors in mongrel dogs were antagonized using the selective antagonist $CGRP_{8-37}$ (400 µg in 30 milliliters (ml) of saline bolus, then 2.6 µg/kg/min for 15 min). Plasma CGRP levels measurements were performed by sampling the blood of the dogs. Blood samples (2.5 ml) were withdrawn from arterial, venous, and coronary sinus catheters. After sampling, catheters were flushed with heparanized saline. Samples were centrifuged at 1600 times gravity (g) for 20 minutes at 4° Celcius (C). Plasma was then separated and stored at −20° C. until analysis. Plasma (0.5 ml) was used to extract CGRP by addition of 0.8 ml of ethanol. The mixture was centrifuged at 1600 g for 20 minutes. After removing the supernatant, the extracted samples were air dried at room temperature overnight and then stored at 4° C. Immediately prior to assay, dried samples were reconstituted with assay buffer following manufacturer's instructions (Peninsula Labs) and assayed for CGRP by radioimmunoassay (RIA) CGRP antiserum, code RAS 6012, was used. The dynamic assay range was 1–128 picograms (pg) per 300 microliters (µL) of sample. Stimulation with HNO/NO⁻ donors and diagnostic tests were performed as described above in Example 1.

Figure 6:
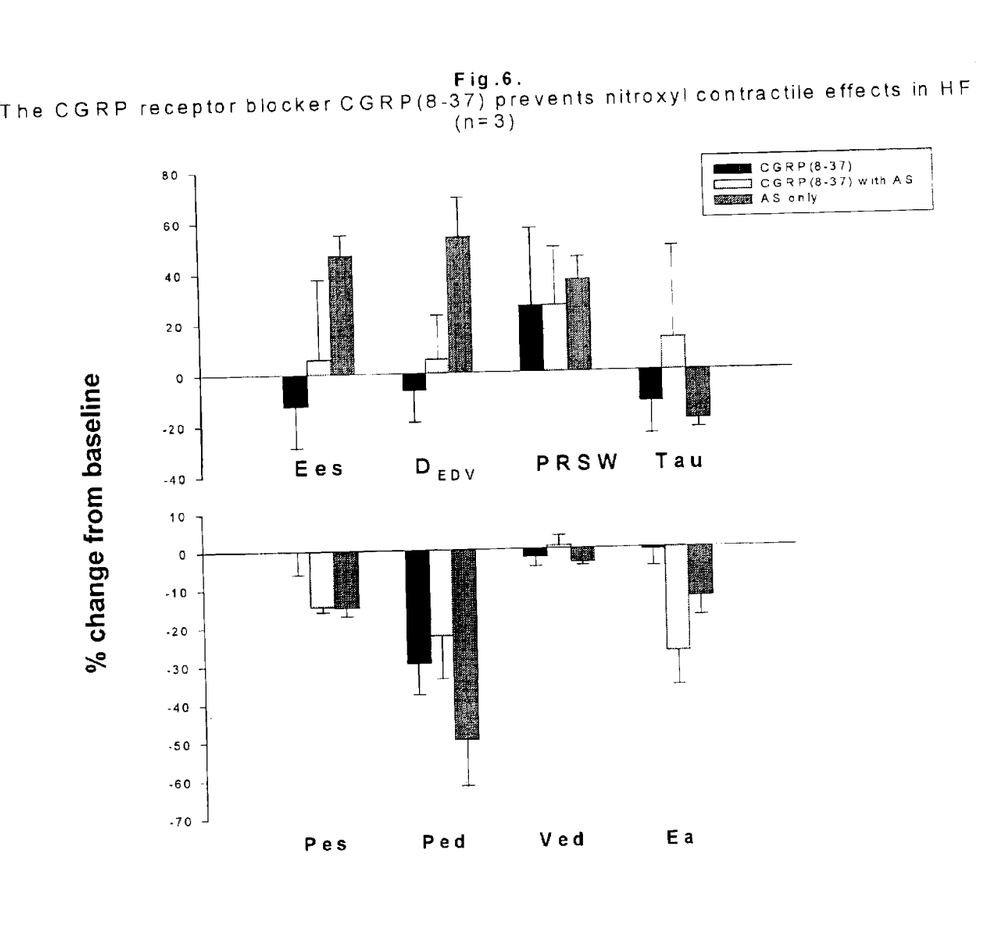
FIG. 6 shows the percentage change from a baseline for several diagnostic tests of hearts of conscious dogs experiencing heart failure (HF) resulting from the administration of calcitonin gene-related peptide$_{8-37}$ (CGRP$_{8-37}$), administration of CGRP$_{8-37}$ in combination with AS, and administration of AS alone. The diagnostic tests included Ees, $D_{EDV}$, PRSW, tau, Pes, end diastolic pressure (Ped), end diastolic volume (Ved), and Ea.

With reference to FIG. 6, administration of the selective CGRP antagonist $CGRP_{8-37}$ resulted in a modest negative inotropic effect during heart failure as measured by Ees. This result was not unexpected given that CGRP is known positive inotrope. Doggrell, Expert Opin. Investig. Drugs, 10:1131–8 (2001). More interestingly, $CGRP_{8-37}$ effectively prevented the HNO/NO⁻-mediated, positive inotropic effect of Angeli's salt as is illustrated by a comparison of the Ees data resulting from the combined administration of $CGRP_{8-37}$ and Angeli's salt with the results observed from administration of Angeli's salt alone. These results illustrate that the positive inotropy of HNO/NO⁻ is caused by stimulating release of CGRP, which is a nonadrenergic/noncholinergic (NANC) neuromodulator.

Figure 7:
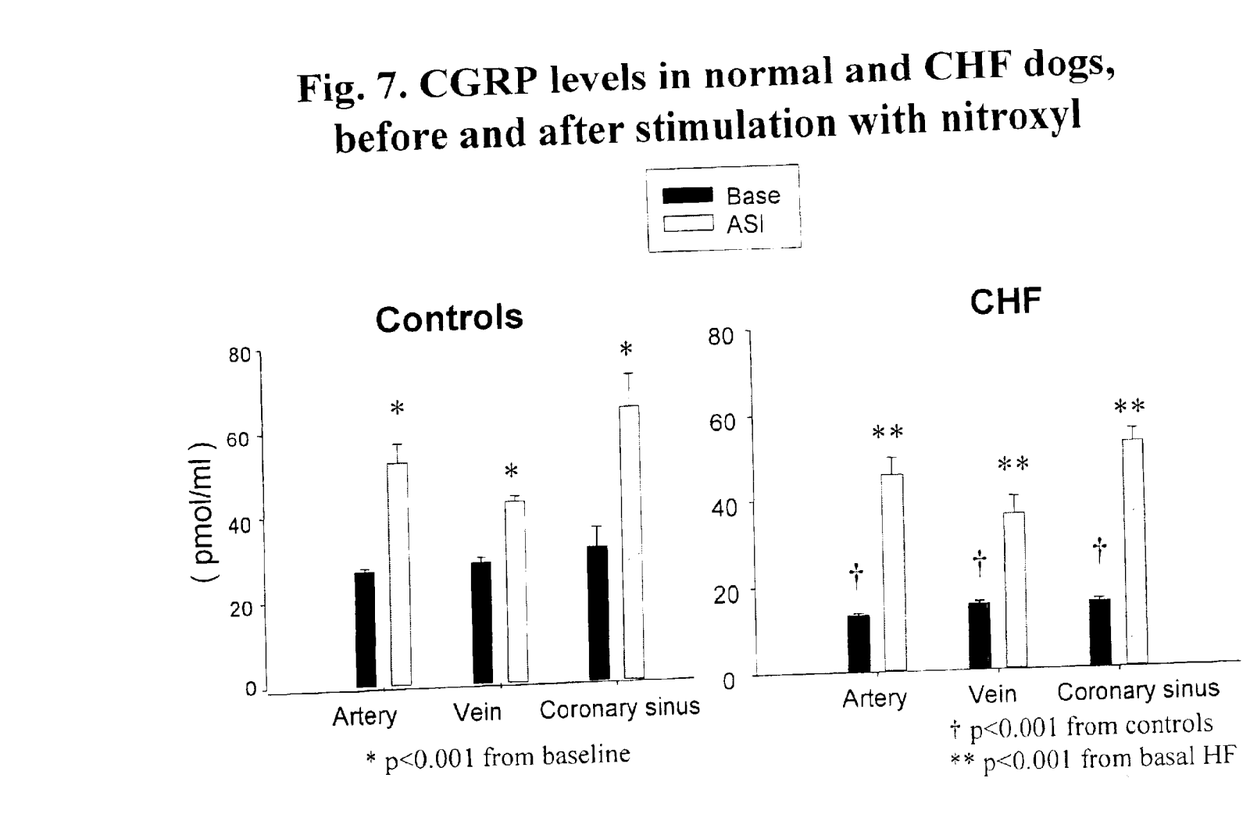
FIG. 7 shows the blood plasma CGRP levels in picomoles (pmol) per milliliter (ml) in the artery, vein, and coronary sinus of normal conscious dogs (controls) and conscious dogs experiencing heart failure.

This is supported by the data illustrated in FIG. 7, which show that blood plasma CGRP levels were increased by administration of the HNO/NO⁻ donor Angeli's salt in both normal and heart failure conditions. A sensitive and specific radioimmunoassay (RIA) was used to study blood plasma levels of CGRP in normal and in CHF dogs, both in basal and stimulated conditions (after administration of AS, DEA/NO and nitroglycerin). The basal mean plasma levels of CGRP were 23, 24.5 and 27 pg/ml in the artery, vein, and coronary sinus of normal dogs, respectively. These levels were significantly reduced in all vascular compartments in CHF dogs. 13.3±0.7, 14.3±1.4, and 14±0.6 pg/ml in artery, vein, and sinus, respectively. When stimulated with the HNO/NO⁻ donor AS, plasma CGRP levels increased substantially in both normal and CHF dogs (FIG. 7). In contrast, stimulation with DEA/NO and nitroglycerin failed to significantly increased CGRP levels. These data clearly show that HNO/NO⁻ directly stimulates the release of CGRP

EXAMPLE 3

This example demonstrates that HNO/NO⁻ effectively increases contractility even when administered to a subject receiving beta-antagonist therapy.

Figure 8:
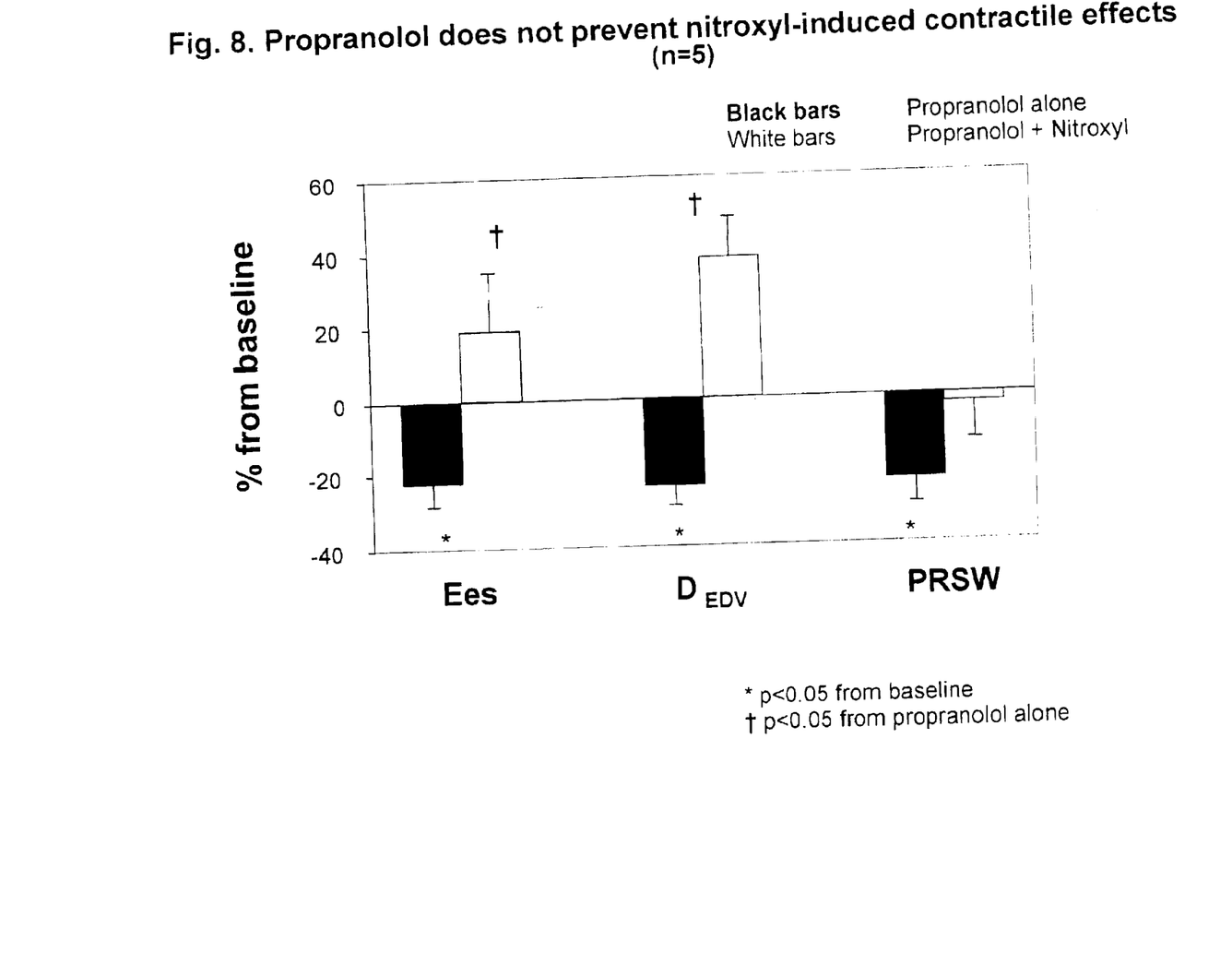
FIG. 8 shows the percentage change from a baseline for several diagnostic tests of hearts of normal conscious dogs, which dogs were under beta-antagonist therapy with propranolol, resulting from administration of the HNO/NO⁻ donating compound AS The tests included Ees, $D_{EDV}$, and PRSW.

As illustrated in FIG. 8, administration of the HNO/NO⁻ donor Angeli's salt (as described in Example 1) to a normal subject that is receiving beta-antagonist therapy (propranolol, 2 milligrams/kg in bolus) caused an increase in contractility as indexed by Ees and $D_{EDV}$ This increase was observed despite the propranolol-induced reduction in myocardial performance Similar results were obtained in one heart failure subject (data not shown)

The above-described examples merely provide particular embodiments of the provided method They are not intended to be limiting in any way Moreover, although embodiments of the method provided have been described herein in detail, it will be understood by those of skill in the art that variations may be made thereto without departing from the spirit of the invention or scope of the appended claims.

We claim:

1. A method of treating heart failure comprising:
administering to a subject experiencing heart failure, a therapeutically effective dose of at least one nitroxyl donating compound and at least one positive inotropic compound, wherein the dose is effective to increase myocardial contractility.

2. The method of claim 1, wherein the positive inotropic compound comprises a beta-adrenergic receptor agonist.

3. The method of claim 2, wherein the beta-adrenergic receptor agonist comprises a selective beta-1 adrenergic receptor agonist.

4. The method of claim 3, wherein the selective beta-1 adrenergic receptor agonist comprises dobutamine.

5. The method of claim 2, wherein the beta-adrenergic receptor agonist comprises dopamine or isoproterenol.

6. The method of claim 2, wherein the beta-adrenergic receptor agonist comprises a selective beta-2 adrenergic receptor agonist.

7. The method of claim 2, wherein the beta-adrenergic receptor agonist comprises an agonist not selective for a particular beta-adrenergic receptor.

8. The method of claim 1, wherein the nitroxyl donating compound comprises a compound having the formula wherein J is an organic or inorganic moiety, M⁺ˣ is a pharmaceutically acceptable cation, wherein x is the valence of the cation, a is 1 or 2, b and c are the smallest integers that result in a neutral compound, and wherein the compound releases the nitroxyl under physiological conditions.

9. The method of claim 8, wherein the nitroxyl donating compound comprises IPA/NO.

10. The method of claim 8, wherein the nitroxyl donating compound comprises a derivative or analog of IPA/NO.

11. The method of claim 8, wherein the nitroxyl donating compound comprises Angeli's salt.

12. The method of claim 1, wherein the nitroxyl donating compound comprises Piloty's acid.

13. A method of treating heart failure comprising:
administering to a subject experiencing heart failure, a therapeutically effective dose of at least one nitroxyl donating compound, wherein the nitroxyl donating compound comprises a compound having the formula wherein J is an organic or inorganic moiety, $M^{30\ x}$ is a pharmaceutically acceotable cation, wherein x is the valence of the cation, a is 1 or 2, b band c are the smallest integers that result in a neutral compound, and wherein the comoound releases the nitroxyl under physiological conditions, and wherein the nitroxyl donating compound comprises IPA/NO.

14. A method of treating heart failure comprising:
administering to a subject experiencing heart failure, a therapeutically effective dose of at least one nitroxvl donating compound, wherein the nitroxyl donating compound comprises Piloty's acid.

15. A method of treating heart failure comprising:
administering to a subject experiencing heart failure and receiving beta-adrenergic receptor antagonist therapy, a therapeutically effective dose of at least one nitroxyl donating compound, wherein the dose is effective to increase invocardial contractility, wherein the nitroxvl donating compound comprises a compound having the fomiula wherein J is an organic or inorganic moiety, $M^{30\ x}$ is a pharmaceutically acceptable cation, wherein x is the valence of the cation, a is 1 or 2, b and c are the smallest integers that result in a neutral compound, and wherein the compound releases the nitroxyl under physiological conditions, and wherein the nitroxyl donating compound comprises IPA/NO.

16. A method of treatina heart failure comorising:
administering to a subject experiencing heart failure and receiving beta-adreneraic receptor antagonist therapy, a therapeutically effective dose of at least one nitroxyl donating compound, wherein the dose is effective to increase myocardial contractility, and wherein the nitroxyl donating compound comprises Piloty's acid.

* * * * *